(12) United States Patent
Horvat et al.

(10) Patent No.: US 7,654,968 B1
(45) Date of Patent: Feb. 2, 2010

(54) PLACENTAL BLOOD EXTRACTOR

(76) Inventors: Branimir L. Horvat, 3307 Clark Rd., Sarasota, FL (US) 34242; Nevenka Horvat, 3307 Clark Rd., Sarasota, FL (US) 34242

( * ) Notice: Subject to any disclaimer, the term of this patent is extended or adjusted under 35 U.S.C. 154(b) by 228 days.

(21) Appl. No.: 11/495,510

(22) Filed: Jul. 28, 2006

(51) Int. Cl.
*A61B 5/00* (2006.01)
*B65D 81/00* (2006.01)
(52) U.S. Cl. ............................ 600/573; 600/578
(58) Field of Classification Search ............... 600/573; 604/6.09, 317, 403; 606/120
See application file for complete search history.

(56) References Cited

U.S. PATENT DOCUMENTS

| | | | | |
|---|---|---|---|---|
| 4,014,329 A | * | 3/1977 | Welch et al. | 604/6.09 |
| 5,053,025 A | * | 10/1991 | Knippscheer | 604/317 |
| 5,114,672 A | * | 5/1992 | Knippscheer et al. | 435/1.1 |
| 5,342,328 A | | 8/1994 | Grossman et al. | |
| 5,356,373 A | * | 10/1994 | Dracker | 604/4.01 |
| 5,415,665 A | | 5/1995 | Hessel et al. | |
| 5,520,699 A | | 5/1996 | Hessel et al. | |
| 5,575,795 A | | 11/1996 | Anderson | |
| 5,690,646 A | * | 11/1997 | Gruenberg | 606/120 |
| 5,919,176 A | * | 7/1999 | Kuypers et al. | 604/317 |
| 6,059,794 A | | 5/2000 | Webb | |
| 6,302,854 B1 | * | 10/2001 | Paderni | 600/573 |
| 6,491,682 B2 | * | 12/2002 | Paderni | 604/541 |
| 7,118,559 B2 | * | 10/2006 | Toomey | 604/403 |

* cited by examiner

*Primary Examiner*—Max Hindenburg
*Assistant Examiner*—Adam J Eiseman
(74) *Attorney, Agent, or Firm*—Frank A. Lukasik

(57) ABSTRACT

A placental blood extractor consisting of an outside box having a plurality of plastic bags mounted within the top and bottom sections of the box and having an opening in the bottom section, a sterile bag having a central closure on a first side and a leader for an umbilical cord on a second side for holding a placenta mounted between the top and bottom plastic bags and a collector of blood system attached to the opening in the bottom, the collector of blood system consists of a pump, a manometer, a computer and a vibrator for gentle shaking of the collector of blood system.

1 Claim, 10 Drawing Sheets

| Bags | Timing in sec. | | | | | | | | | | | |
|---|---|---|---|---|---|---|---|---|---|---|---|---|
| | 30 | 30 | 30 | 30 | 30 | 30 | 30 | 30 | 30 | 30 | 30 | 30 |
| | Elapsed time in min. | | | | | | | | | | | |
| | 1 | 1.5 | 2 | 2.5 | 3 | 3.5 | 4 | 4.5 | 5 | 5.5 | 6 | |
| 1 | <u>90</u> | 90 | 90 | 90 | 90 | <u>105</u> | 105 | 105 | 105 | 105 | <u>120</u> | 120 |
| 2 | (20) | <u>80</u> | 80 | 80 | 80 | 80 | <u>95</u> | 95 | 95 | 95 | 95 | <u>110</u> |
| 3 | (20) | (20) | <u>70</u> | 70 | 70 | 70 | 85 | <u>85</u> | 85 | 85 | 85 | 85 |
| 4 | (20) | (20) | (20) | <u>65</u> | 65 | 65 | 65 | 75 | <u>75</u> | 70 | 70 | 70 |
| 5 | (20) | (20) | (20) | (20) | <u>60</u> | 60 | 60 | 60 | 60 | <u>65</u> | 65 | 65 |

| Bags | Timing in sec. | | | | | | | | | | | |
|---|---|---|---|---|---|---|---|---|---|---|---|---|
| | Elapsed time in min. | | | | | | | | | | | |
| | 6.5 | 7 | 7.5 | 8 | 8.5 | 9 | 9.5 | 10 | 10.5 | 11* | 11.5 | 12 |
| | 30 | 30 | 30 | 30 | 30 | 30 | 30 | 30 | 30 | 30 | 30 | 30 |
| 1 | 120 | 120 | 120 | 120 | 120 | 120 | 120 | 120 | 120 | 120 | 120 | 120 |
| 2 | 110 | 110 | 110 | <u>120</u> | 120 | 120 | 120 | 120 | 120 | 120 | 120 | 120 |
| 3 | <u>100</u> | 100 | 100 | 100 | <u>110</u> | 110 | 110 | <u>120</u> | 120 | 120 | 120 | 120 |
| 4 | 70 | <u>95</u> | 95 | 95 | 95 | <u>105</u> | 105 | 105 | <u>120</u> | 120 | 120 | 120 |
| 5 | 65 | 65 | <u>85</u> | 85 | 85 | 85 | <u>100</u> | 100 | 100 | <u>120</u> | 120 | 120 |

( ) indicates the pressure at the initiation of the PBE operation (20 mmHg)

<u>__</u> Underlined number indicates the compression chamber which is being pressurized at that time.

\* After this time no pressurization is being done and only negative pressure from COB is being exerted on the umbilical cord. If flow of blood is continuing, this 2 time of extraction of the blood may be delayed by the operator until no more blood is extracted.

FIG. 13

PLACENTAL BLOOD EXTRACTOR

FIELD OF THE INVENTION

This invention relates broadly to medical instruments, and more particularly, this invention relates to an umbilical cord blood extractor which extracts placental blood from a cut section of umbilical cord after the placenta is delivered after the birth of the child.

STATE OF THE ART

The umbilical cord serves as the conduit between a mother and a fetus developing in the womb of the mother. Nutrients and oxygen within the blood of the mother pass through the umbilical cord to the fetus. Immediately after a baby is born, the umbilical cord is clamped to stop the flow of blood through the umbilical cord, then the placenta is expelled from the mother's uterus.

A quick method of sampling blood from the cord is to manually milk blood from the section of cut cord; i.e., to squeeze the section of cut umbilical cord by hand to rapidly and thoroughly remove blood from the cord. However, this is not usually practical. The umbilical cord is coated with various fluids, e.g., vaginal blood, amniotic fluid and Wharton's gel, making the cord slippery and hard to handle. Furthermore, it is desirable to minimize contact between health care workers and such fluids. In fact, federal law and an association of operating room nurses have mandated protecting health care workers from blood born pathogens.

A number of devices have been disclosed for taking a sample of blood from an umbilical cord which do not require manually milking the cord. U.S. Pat. No. 5,575,795 to Anderson discloses an umbilical cord holder having an elongate portion with a curved open trough and clamps at either end of the elongate portion. A health care worker places the umbilical cord into the trough and seals the ends of the umbilical cord with the clamps. While holding the elongate portion, the practitioner inserts a needle through the open trough and into the cord and a syringe is operated to withdraw blood from the cord.

U.S. Pat. No. 5,860,989 to Webb discloses umbilical cord blood extractor which includes a lower tray for receiving the cord and an upper lid for squeezing the cord, each having a hinged end and a free end. The lower tray and the upper lid are connected by a live hinge at their hinged ends. The lower tray is further provided with a longitudinal trough and a distal blood reservoir for collecting blood. A blood collection needle is preferably provided in the lower tray at a lower portion of the reservoir. The upper lid is formed with a longitudinal protrusion sized such that when the upper lid is rotated about the hinge, up and toward the lower tray, the plunger enters into the trough.

U.S. Pat. No. 6,059,794 to Webb discloses an umbilical cord blood extractor includes a lower tray for receiving the cord and an upper lid for squeezing the cord. The lower tray is provided with a longitudinal trough and a distal blood reservoir for collecting blood. The trough is closed at its proximal end and opens into the reservoir at its distal end. A blood collection needle is preferably provided in the lower tray at a lower portion of the reservoir. The upper lid has a longitudinal protrusion (plunger) sized such that when the upper lid is rotated toward the lower tray, on the pivots or at the hinge, the plunger enters into the trough and squeezes a section of the umbilical cord located therein.

SUMMARY OF THE INVENTION

It is therefore an object of the invention to provide an apparatus for rapidly extracting blood from a placenta and an umbilical cord.

It is another object of the invention to provide an apparatus which minimizes contact between a practitioner and blood being extracted from an umbilical cord.

It is a further object of the invention to provide an apparatus which is inexpensive and easy to manufacture and which extracts blood from an umbilical cord and placenta.

A still further object of the invention is to dramatically increase the amount of the extracted blood by pressurizing the placenta and delivering this blood to the umbilical cord where it would be collected.

In accord with these objects which will be discussed in detail below, an umbilical cord blood extractor is provided and broadly comprises means for receiving the cord, means for extracting the cord, and preferably for collecting the blood from the cord. Umbilical cord blood has been collected for many different reasons, one of which is that it contains significant number of stem cells. They are used in many therapeutic and experimental procedures. Obtaining the placental blood is a cumbersome problem as well as results in rather small amounts of blood being collected. The instant process is presently done by "milking" the umbilical cord. The usual amount of blood obtained through this process is from 70 cc to 120 cc.

The proposed Placental Blood Extractor (PBE) for collection of umbilical and placental blood is very simple in operation. It is also composed of few parts, easily maintained. The invention comprises an outside box, a plastic bag lining the outside box, a pump for exerting air pressure in the plastic bags, a valve between the pump and bag, a Manometer for determining the pressure to be applied, Sterile bags where the placentas are placed prior to the pumping procedures with a tube for insertion of the umbilical cord, and a regulatory computer for maintaining the pressure as the blood is being extracted from the placenta. In the box for collection of the blood, a negative pressure is used to facilitate the extraction of blood from the umbilical cord.

BRIEF DESCRIPTION OF THE DRAWINGS

FIG. 13, shows the suggested pressure sequence in the bags for pressurization of a placenta.

DETAILED DESCRIPTION OF THE INVENTION

Figure 1:
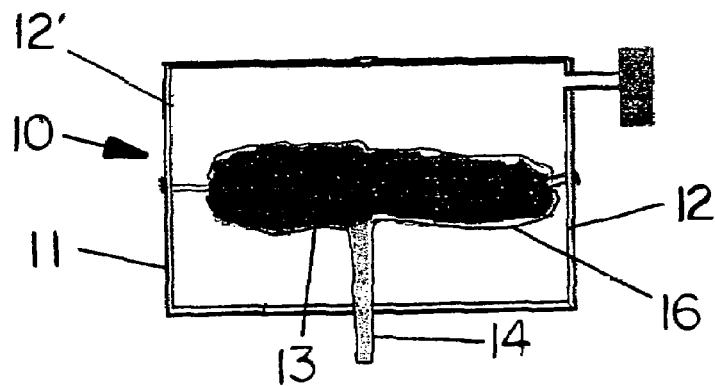
FIG. 1 is a side view of the placenta in a single pressure bag of a first embodiment of the invention.

The instant invention, a placental Blood Extractor (PBE), for collection of the umbilical and placental blood is a very simple operation, it is composed of the Placental Blood Extractor (PBE) 10 and the Collector of Blood 27 (COB). The entire system is composed of relatively few, easily maintained parts. The system consists of the outside box 11, (FIGS. 1, 2, 7 and 8). This box 11, is round in shape and, depending on whether one should serve all processed placentas, or more boxes are produced for different sizes of the placenta. Thus if constructed larger, then it can serve most of the placentas. When different sizes are used, the sizes are from six inches in diameter to more than twelve inches in diameter.

The box 11 is round in shape and composed of two parts, the lower box 11 and the upper box 11' which will be closed for compression of the placentas 13. The lower box 11 has an opening 23 where the umbilical cord 14 is lead outside of the compression area. A plastic bag 12, lines the outside box 11.

Figure 7:
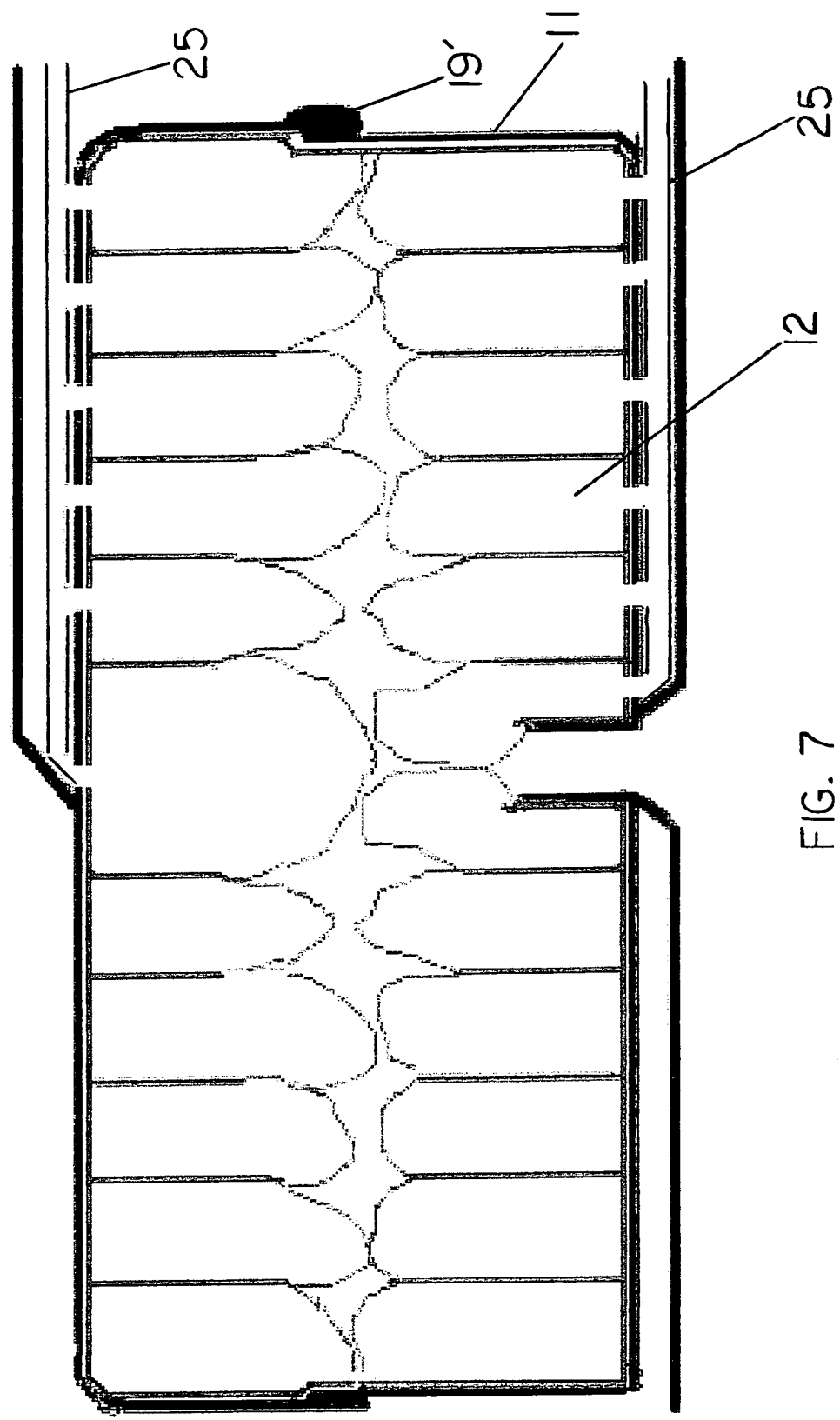
FIG. 7 is a side view of a PBE with six inflated compression chambers without placenta.

The plastic bag 12 may be constructed of one or several separate bags, all concentric. In the case of one single bag 12, one channel for the upper and one channel for the lower part of the bag 12 is used. In the case of more than one bag 12, each separate upper and lower corresponding bags (FIGS. 9-11) has a separate inflation channel. Thicker plastic bags 12 line walls of the outside box 11 and are also attached to each other in a concentric fashion. They are identical in the upper part of PBE as they are in the lower part of PBE with the exception of the very central inflation bag 22 which has a central part for the insertion of the umbilical cord 13 outside the firm compression box 11. The tops of the lower bags and lower parts of the upper bags have a thinner plastic which serves the function of inflation of the bags and compression of the placentas 13. When there is no placenta in the PBE, the inflated thinner plastics meet each other (FIG. 7). When not inflated, placentas 13 can be placed into the PBE and the box 11 can be closed.

Figure 2:
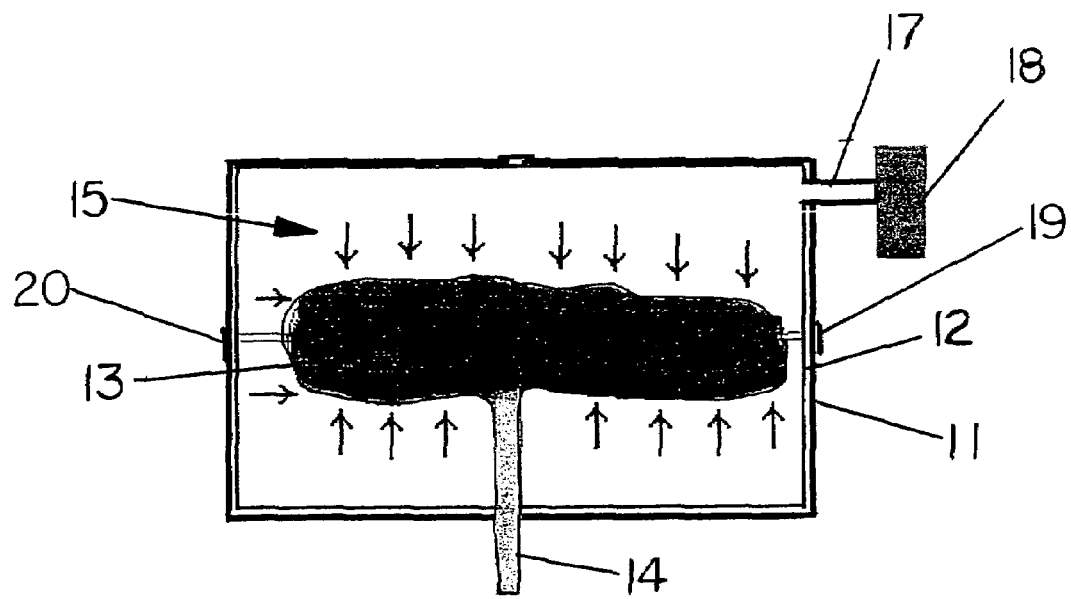
FIG. 2 is a side view of a single pressure bag having pressure exerted to the bags of a single pressure bag embodiment of the invention.

In FIGS. 1 and 2, a pump, manometer and computer system 18 provide the pressure for the plastic bags 12. In the case of one single bag 12, this channel becomes separated when entering PBE to be able to inflate both sides of the bag 12, the upper and lower ones. When more than one inflation bag is used, each has a separate channel from the pump 18 and this channel divides when entering PBE to be able to identically pump the upper part and the lower part of the inflation bag 12.

FIGS. 1 and 2 also show the pressure (arrows 15) squeezing the blood out of the placenta 13. Connection 17 is used to apply the pressure from pump, manometer, computer system 18 Hinge 19 and lock 20 hold the two sections of the box 11, 11' together.

When more than one bag is used, there are several valves 25 (connectors) (FIGS. 3, 4 and 9-11) controlling the inflation sequence, as many as there are inflation bags. The two way valves 25 control either pumping or deflating the bags 12, 12' and provide the information to the computer (not shown) about the achieved pressure on the bags 11, 11'.

Figure 3:
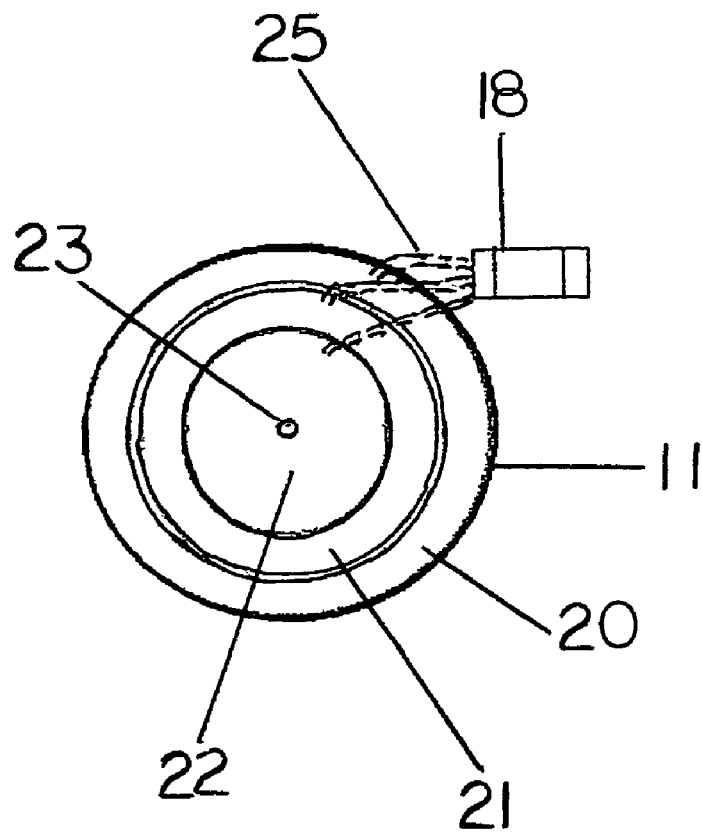
FIG. 3 is a top perspective view of the PBE having three concentric bags for pressurization and the area where the umbilical cord is placed.
Figure 4:
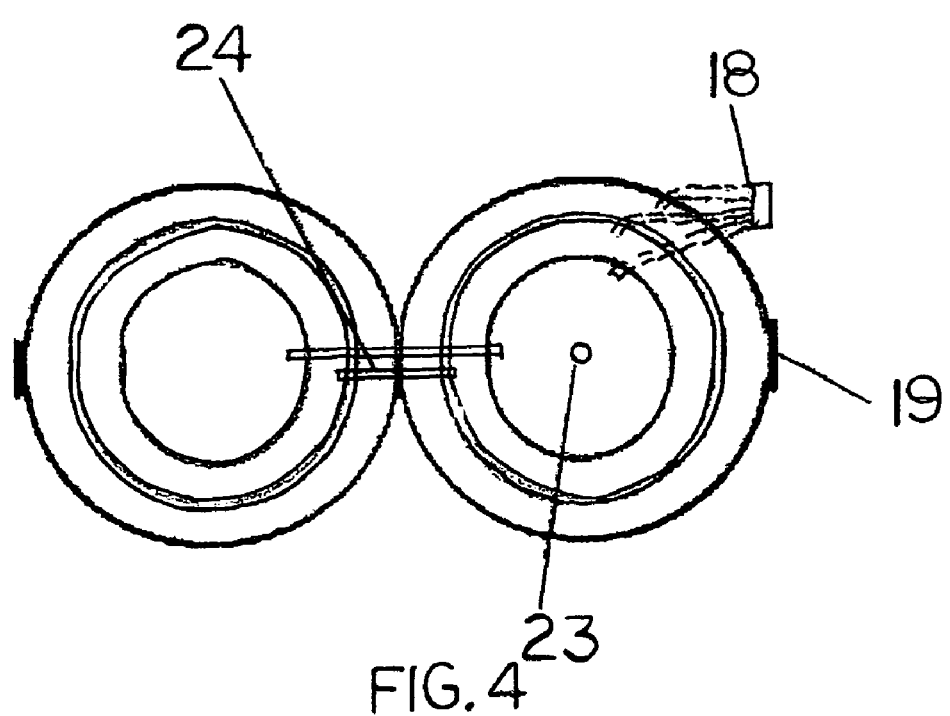
FIG. 4 is a top perspective view of an open PBE apparatus having three concentric bags for pressurization.

FIGS. 3 and 4 show a PBE having three concentric bags 20, 21, and 22 and the area where the leader 14' for the umbilical cord 14 is placed. Control system 18, including a pump, manometer, and computer is connected to the first peripheral bag 20, second peripheral bag 21 and third peripheral bag 22 through valves 25. The manometer determines the pressure to be applied. This manometer is connected by a channel to the channel for pumping the inflation bags prior to the valves 25 and provides the computer about the achieved pressures in the bags.

Figure 5:
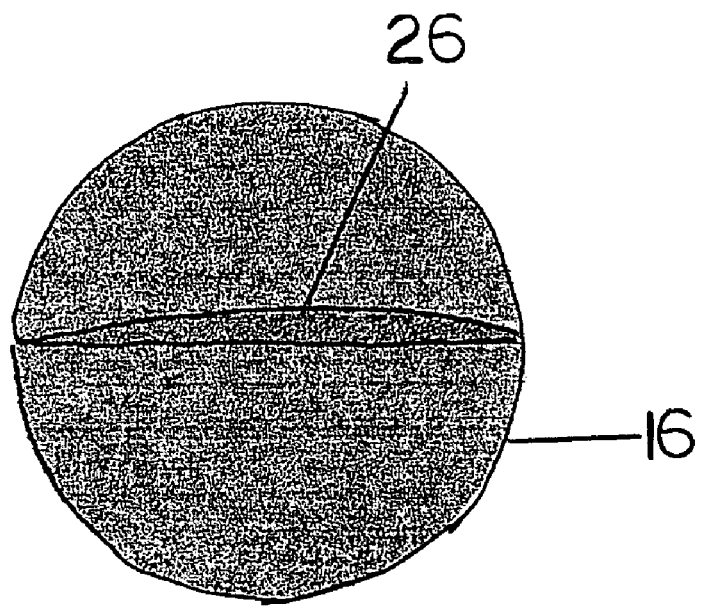
FIG. 5 is a top perspective view of the sterile bag for placement of the placentas.
Figure 6:
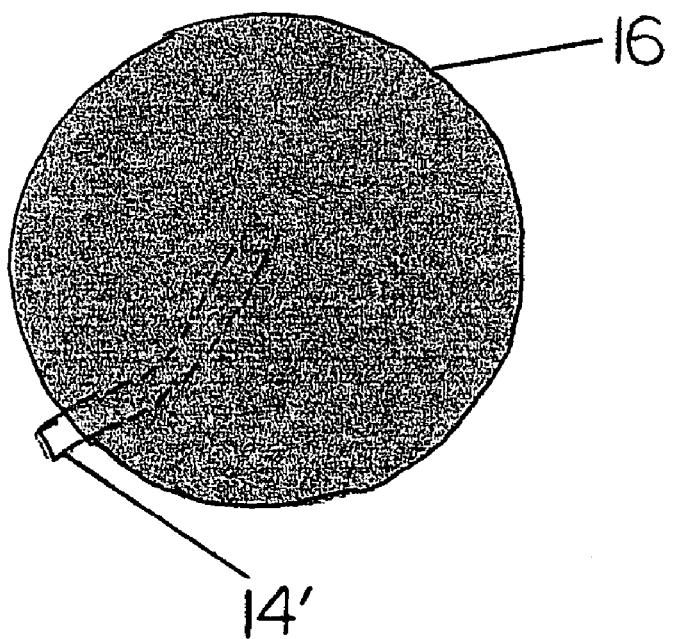
FIG. 6 is a bottom perspective view of the sterile bag for placement of the placentas.

FIG. 5 is a top view of a sterile bag 16 for placement of the placenta 13 having a central closure 26. FIG. 6 is an opposite view showing the leader 14' for the umbilical cord 14. These are commercially available sterile bags for placement of the placentas 13 prior to placing them in the PBE. These bags will minimize the handling of the placentas 13 by the operator.

Figure 8:
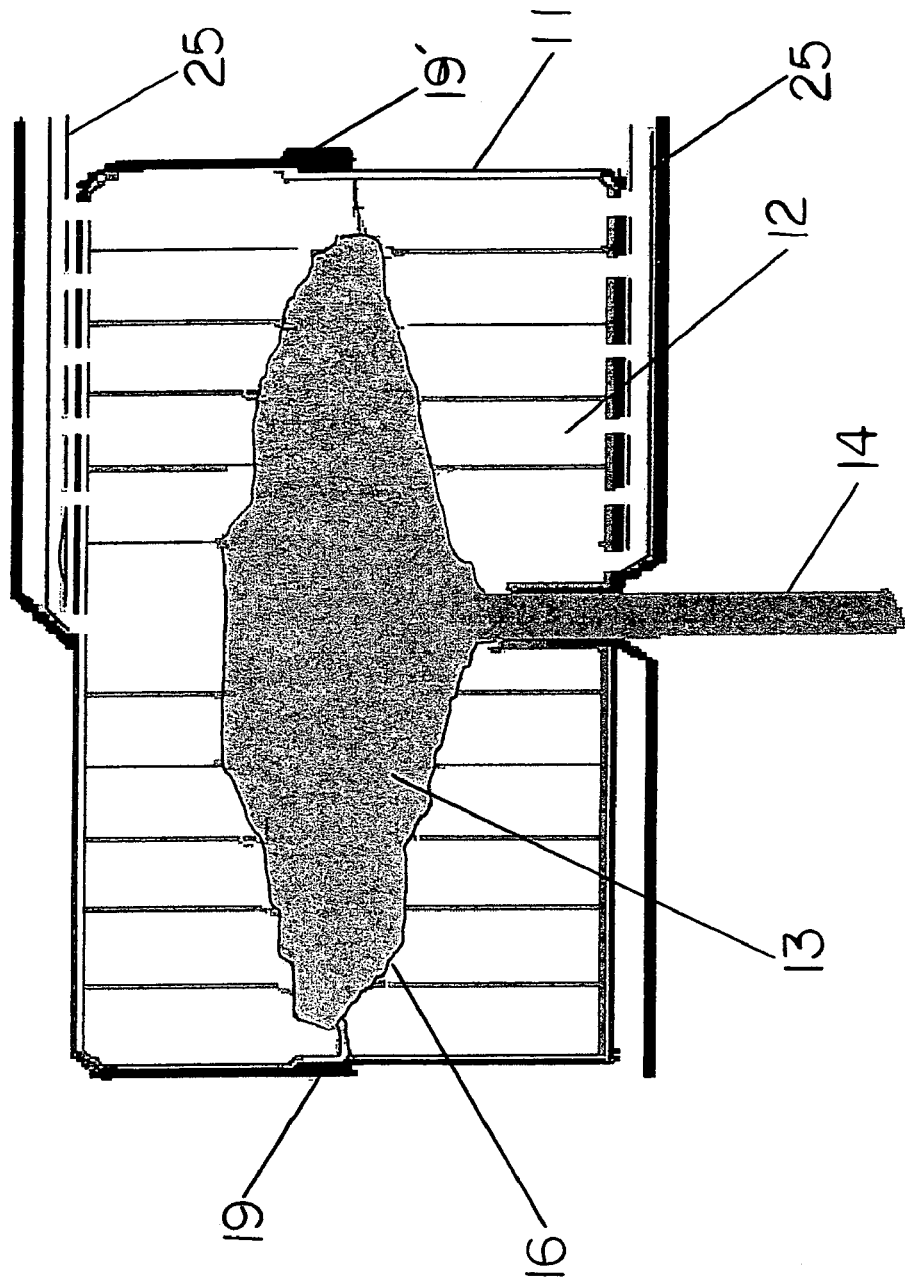
FIG. 8 is a side view of a PBE with six inflation chambers with a placenta.

FIG. 6 shows a PBE with six inflated compression chambers 12 without a placenta 13. FIG. 8 shows a PBE with six inflated compression chambers 12 with a placenta 13.

Figure 9:
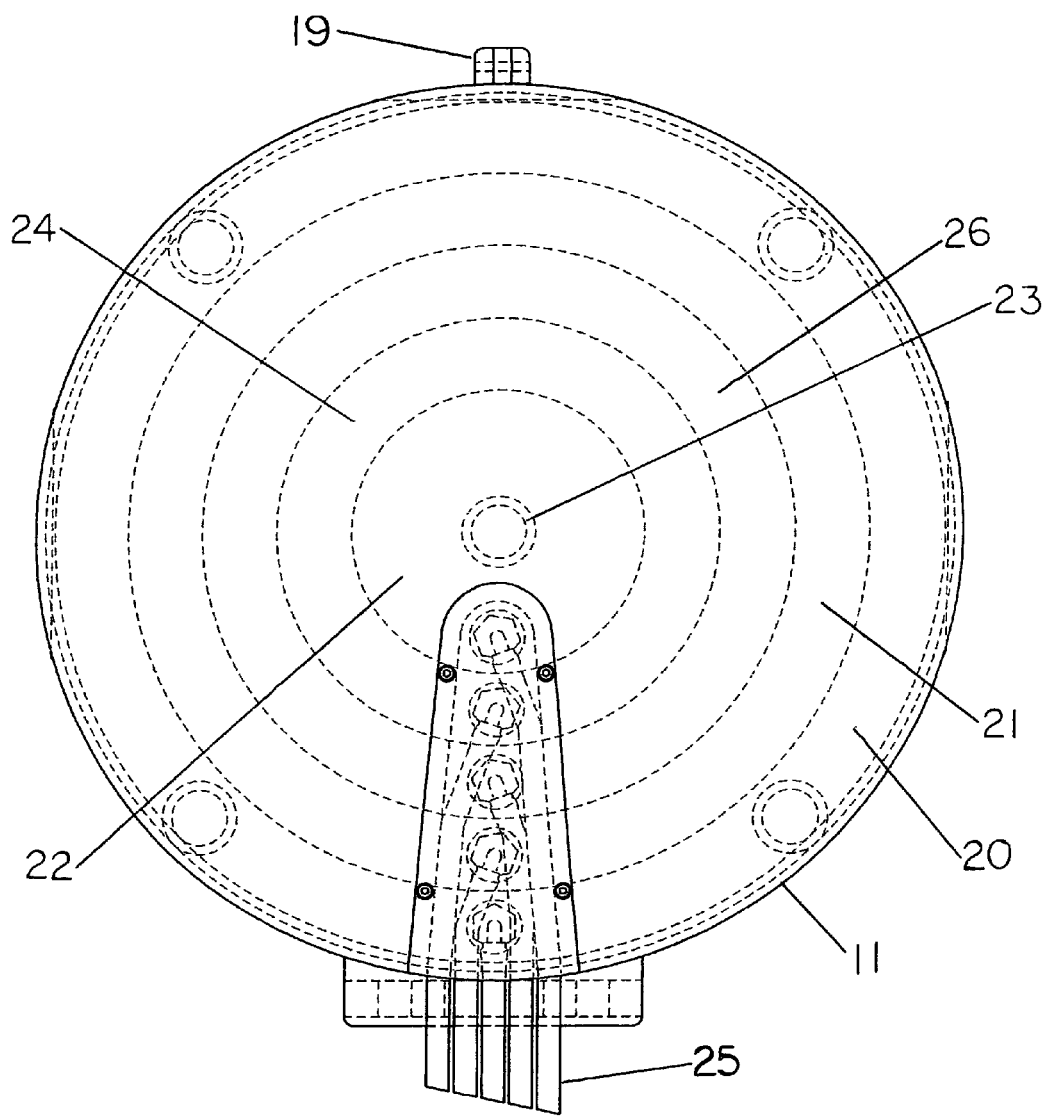
FIG. 9 is a top view of a PBE with five inflation chambers.
Figure 10:
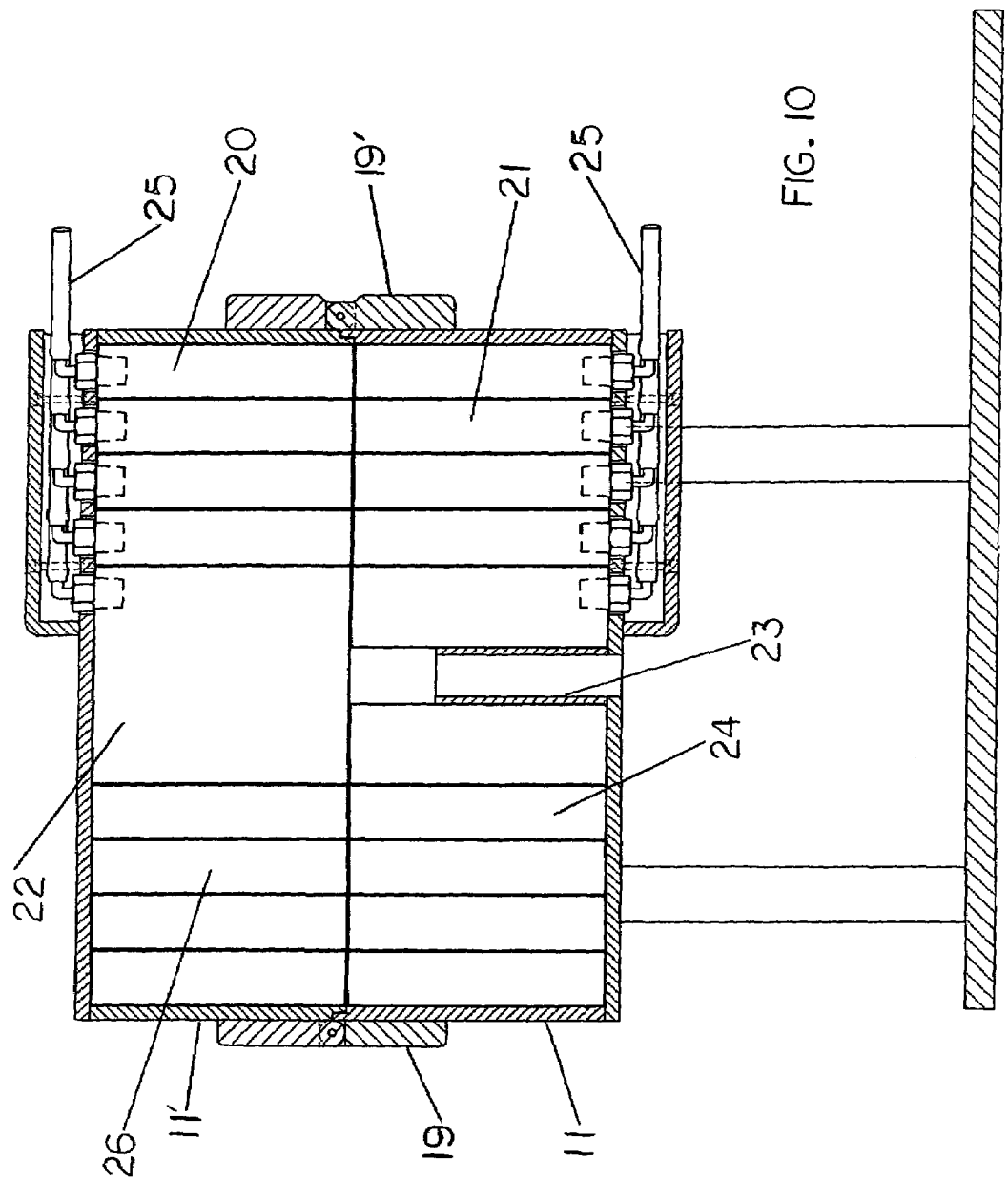
FIG. 10 is a side view, in section, of a PBE.
Figure 11:
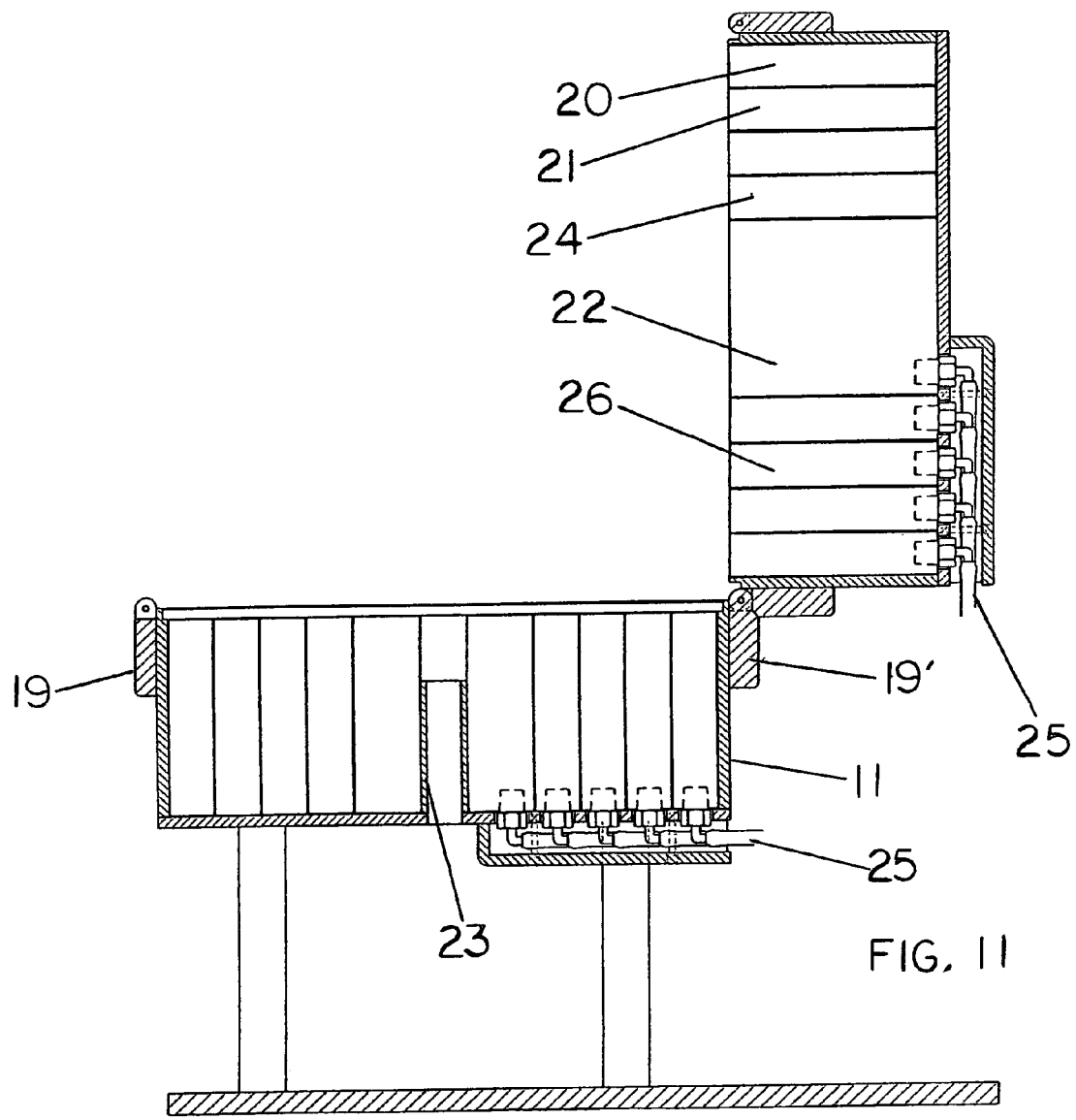
FIG. 11 is a side view, in section, of an open PBE.

FIG. 9 is a top view of a PBE with five inflation chambers. FIG. 10 is a side view, in section of a PBE with five inflation chambers and FIG. 11 shows an open PBE. FIG. 11 is a side view, in section, with the top 11' of the box 11 in open position. Outside box 11, 11' is lined with five concentric inflation bags 20, 21, 24, 26 and central bag 22. Hinges 19 and 19' hold the two sections of the box 11 and 11' together when closed. Valves 25 are attached to each of the inflation bags. A leader 23 is provided for the umbilical cord 14.

Figure 12:
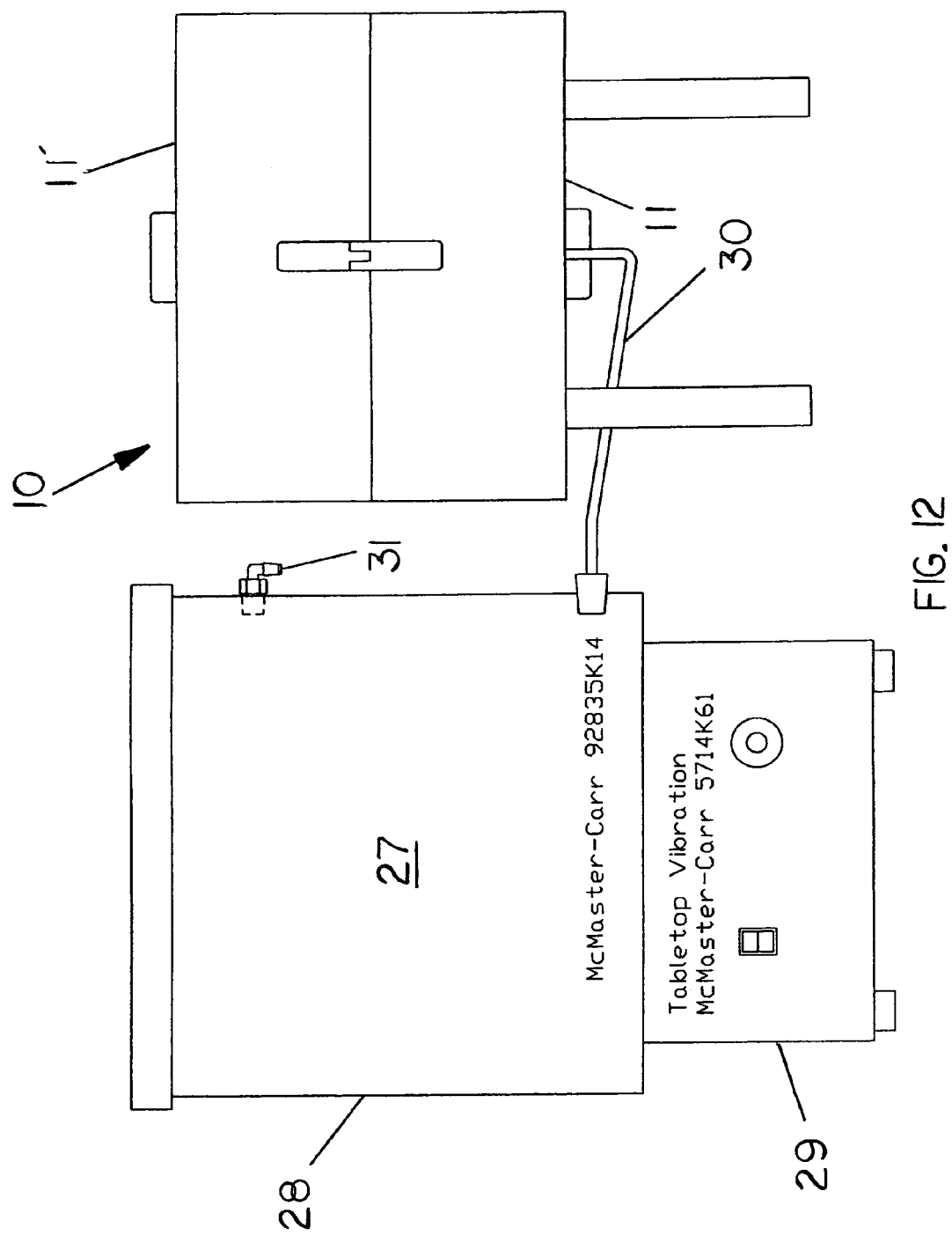
FIG. 12 is a side view of the PBE system.

FIG. 12 is a side view of the PBE System.

The applied pressure on the compression bags should be in the low levels as per determination of the operators. As a general rule, no more than 200 mm Hg pressure should be applied. Usual maximal pressure should be between 120 to 150 mm Hg which is sufficient to extract most of the blood from the placenta into the umbilical cord.

The second part of the Placental Blood Extractor is the Collector of Blood (COB) 27. Transparent, firm plastic box 28 for insertion of the sterile collection bags for the blood serve the purpose of being able to decrease the pressure in this box 28 and facilitates the collection of the blood for its collection. This low negative pressure facilitates the flow of blood from the umbilical cord 13 to the sterile collection bag where anti-coagulants are present to prevent any coagulation of the collected blood. The transparent box 28 serves the purpose so that the operator has a continuous visual control of the operation of the equipment. The transparent plastic box 27 has a manometer attached to its wall or at the pump for that purpose. The box 27 is placed on the vibrator 29 mechanism for gentle shaking of the box 27 with the collection sterile bag.

This mechanism gently shakes the transparent firm plastic box 27 and the inserted bag for the collection of blood facilitating the mixing of the anticoagulant with the collected blood. This shaking is present during the entire operation of the collection of the placental and cord blood. A low pressure pump inside the box 27, produces the negative pressure in the box 27, which is transmitted to the collection bag 16 for blood through tube 30. This achieves continuous flow of all blood available in the umbilical cord without damaging the collected cells. It is operated through the computer software designed for that purpose.

A manometer (not shown) measures continuously, the achieved pressure and record it and releases this information to the computer. Due to this information, the computer software is able to maintain the level of pressure if it is changed at any time during the operation of PBE. The computer software then directs the pump to decrease the pressure if it increases during the collection of blood.

The computer software makes the collection of the blood from the placenta and the umbilical cord as short as possible and uniform for the operators. It manages the levels of the pressure applied to different chambers of PBE, time of these pressures and controls the pressure in COB. At the end of the operation, it may issue a report to the operator with all information regarding the collection.

Commercially available sterile tubing, with the sterile needles (plastic or stainless steel) connecting the vessels of the umbilical cord and the commercially available sterile collection bags for the blood collection. The tubing may be slightly modified to be possible to be attached firmly to the transparent plastic box 28 for preservation of the integrity of the air in the box 27. The negative pressure in the box 27 facilitates flow of the blood into the bag.

Operation of the Equipment

Operators of PBE and COB are able to make certain modifications of the operations of PBE and COB. They are allowed to modify the following parts of operation:

a. Total time of the collection aside from the restriction in the further list of these restrictions.

b. Modify the pressures in the different bags for pressurization of the placenta.

c. Negative pressure level in the transparent firm box of COB.

d. Levels of gentle shaking of the COB.

The operators are restricted in making certain modifications of the operations. They are not allowed to modify the following parts of operations:

a. Time of collection should not exceed 20 minutes due to the possible coagulation of the blood in the placenta and the umbilical cord.

b. Reverse the pressure in the bags for pressurization to result in the lower pressures in the peripheral bags and higher and higher in the central ones. This will result in accumulation of blood in the periphery of the placenta and obstruction of the blood to flow toward the umbilical cord.

c. Increase the shaking of COB above the levels suggested by the manufacturer. This may mechanically damage the cells collected in the bag.

Steps in Operation of the Equipment a. Operator visually inspects PBE that all inflation bags are deflated. If this is not the case, the operator deflates the bags through order onto the computer. This part of operation is not recorded as the start of the operation.

b. Prior to handling the placenta, the operator places the sterile collection bag into COB and attaches the modified commercially available kit for connection of the collection bag and the vessels of the umbilical cord. The cover of the plastic or stainless needle for insertion into the umbilical cord is not removed at this point. Operator visually inspects the bag for the presence of the anticoagulant in the bag.

c. When this is completed, the transparent firm plastic box is firmly closed.

d. Mechanism for shaking is tested. If the appropriate, agitation is present, the operator proceeds with the next step.

e. computer is put in the "ON" position and proper time is checked to be properly displayed.

f. At that point, the following information may be entered into the computer:

1. Internal identification of the procedure for this Blood Bank is placed into the computer.
2. Time is automatically entered by the computer at the actual start of operation and the operator does not do this. However, the time of the start of the operation is entered by the computer when the operator starts the operation of collection of the blood.
3. Name of the mother delivering the baby and the placenta is entered.
4. Name of the baby whose placenta is processed is entered. If the name is not known at that time, name like "Baby Boy Smith" is entered.
5. Time of delivery of the baby is entered.
6. Time of delivery of placenta is entered.
7. Weight of the placenta is recorded. The placenta is measured after it is placed into the sterile plastic bag. The placenta may be measured after it is placed into the sterile plastic bag or after the extraction of the blood is done.
8. Diameter and thickness of the placenta is entered. The placenta may be measured after it is placed into the sterile plastic bag or after the extraction of the blood is done.
9. The initial pressure of the most peripheral bag is entered, differentiation of pressures in the consecutive bags is also entered as well as the time for each pressurization. The operator also has a choice to start the operation of PBE as is suggested by the manufacturer (default procedure) aside from the restriction placed by the manufacturer.

g. After the placenta is placed into the sterile plastic bag, the umbilical cord is inserted into the place for the cord. This may be done prior to weighing the placenta and checking the diameter and thickness of the placenta or after the extraction of the blood is finished.

h. When the weighing and measuring of the placenta is done, the sterile plastic bag with the placenta is placed into the PBE and the umbilical cord is lead through the place of PBE designed for that purpose.

i. After that, PBE is closed firmly.

j. At this point, the closed part of the sterile bag designed for the umbilical cord is cut with sterile scissors and the operator in the sterile gloves gently handles the umbilical cord and pulls it from the PBE box.

k. After cleansing the umbilical cord with a disinfecting solution, the sterile needles are firmly inserted into all three umbilical vessels. Distant part of the umbilical cord may be "clamped" after that. In case of anatomic deviation of the number of umbilical vessels, all vessels are inserted after the operator detects this variation.

l. After the final inspection that all this is properly done, the operator starts with the operation of PBE. This will simultaneously start pressurizing the inflation bags, develop negative pressure in COB and the gentle shaking of COB will commence. The operator will be able to see the blood flowing into the sterile bag for the collection of the blood.

FIG. 13 shows the suggested pressures for operation as well as the timing. The negative pressure in COB is 50 mm Hg. Positive pressure sequence in the bags for pressurization of the placenta in this example it is assumed that PBE has five concentric pressurization bags. For designing the software for operation of PBE the pressurizing of the compression chambers will be described. The table shows the pressure levels and time of pressurization of each chamber.

The computer initiates pressurization of all chambers to the level of, e.g., 20 mm Hg, as default procedures suggest. The valve for concurrently pressurizing all chambers is open and valves for individual chambers are closed. Also, the agitator is started as well as the negative pressure of, e.g., −50 mm Hg in COB is commencing. These last two operations will not be addressed again because these functions continue until the end of the function of PBE.

When the compression in all chambers reach 20 mm Hg, the valve for all chambers is closed and the valve for the first chamber is opened and, as FIG. 13 shows, the first chamber (in case of five chambers) is inflated until the pressure of 90 mm Hg is reached.

When the compression in the first chamber reaches 90 mm Hg level, the valve for the first chamber is closed. After 30 seconds, the valve for the second chamber is opened and the second chamber is inflated until the pressure of 80 mm Hg is reached.

When the compression in the second chamber reaches 80 mm Hg level, the valve for the second chamber is closed. After 30 seconds, the valve for the third chamber is opened and the third chamber is inflated until the pressure of 70 mm Hg is reached.

When the compression in the third chamber reaches 70 mm Hg level, the valve for the third chamber is closed. After 30 seconds, the valve for the fourth chamber is opened and the fourth chamber is inflated until the pressure of 65 mm Hg is reached.

When the compression in the fourth chamber reaches 65 mm Hg level, the valve for the fourth chamber is closed. After 30 seconds, the valve for the fifth chamber is opened and the fifth chamber is inflated until the pressure of 60 mm Hg is reached. When the compression in the fifth chamber reaches 60 mm Hg level, the valve for the fifth chamber is closed. Now the cycle of inflation is repeated, but this time at the higher level of pressures. After 30 seconds, the valve for the first chamber is opened and the first chamber is inflated until the pressure of 105 mm Hg is reached. At this point, pressure in the chambers is gradually increased as per schedule in FIG. 13 until the maximum pressure is present in all of the compression chambers.

At that point, no more increase of inflation is being done, however, computer checks, from the first to the fifth chamber that the pressure of 120 mm Hg is being maintained for at lest two minutes. If the pressure is not at that level, additional air is pumped into the chamber and if it is successfully maintained in this level, the next compression chamber is checked, etc. This is continuing until the two minutes of this time elapses. The operator may prolong for a short period of time this two minutes period if the blood continues flowing into the collection bag.

When the extraction of blood from the placenta and umbilical cord is finished (computer may give a warning at that time), and when the operator determines that no more collection is going on, "STOP" command is given. If for any reason the operator does not give this command, the PBE's computer will stop the operation and continues with further steps of closing the blood flowing into the sterile bag for collection of the blood.

When the extraction of the blood is finished, PBE compression bags are deflated. The computer gives a warning prior to that. The operator opens COB and seals the tubes delivering the blood. The needles are removed from the umbilical cord and the placenta is placed into a disposal area. If the measurement and the weight were not done prior to this, it is done now and the placenta is placed for disposal. The sterile bag with the collected blood is appropriately handled for shipping. PBE and COB are cleaned for the next collection and stored after that.

While a preferred embodiment of the present invention has been shown and described, various modifications may be made without departing from the scope of the present invention, and all such modifications and equivalents are intended to be covered.

What is claimed is:

1. A placental blood extractor for collection of umbilical and placental blood, said blood extractor comprising:
    a round outside box, said box having a top section and a bottom section and having an opening in said bottom section,
    a plurality of inflatable compression chambers concentrically mounted within said top section and a corresponding plurality of inflatable compression chambers concentrically mounted within said bottom section, each of said compression chambers having a valve attached thereto,
    a sterile bag for holding a placenta, said bag being mounted between the compression chambers of said bottom section and said top section upon closure of said top and bottom sections, said sterile bag having a central closure on a first side and a leader for an umbilical cord on a second side, said leader mounted within said opening in said bottom section,
    a blood collection system attached to said leader, said system having a transparent, firm plastic box for insertion of the sterile collection bags for the collected blood, said collection bags having commercially available anticoagulates for preventing coagulation of the collected blood, said box having a negative pressure to facilitate the flow of blood from the umbilical cord,
    a pump attached to each of said plurality of compression chambers for sequentially applying pressure to each of said concentrically mounted compression chambers within said top section and said bottom section,
    wherein sequentially applying pressure comprises always having the pressure in the next inwardly central compression chamber lower than in the adjacent outer compression chamber,
    a manometer for determining the pressure to be applied to the compression chambers,
    a computer for maintaining the levels of the pressure applied to different compression chambers and the time of these applied pressures as the blood is being extracted from the placenta; and for controlling the pressure within said system, and
    a vibrator mounted within said system for gentle shaking of said blood collection system.

* * * * *